United States Patent [19]
Katsurada et al.

[11] Patent Number: 5,498,336
[45] Date of Patent: Mar. 12, 1996

[54] LEUKOCYTE-REMOVING FILTER AND LEUKOCYTE-REMOVING APPARATUS FURNISHED THEREWITH

[75] Inventors: Naoki Katsurada, Ashigarakami; Sobei Wakabayashi; Tomoko Hashimukai, both of Fukui; Yoshitaka Omura, Kanagawa, all of Japan

[73] Assignee: Terumo Kabushiki Kaisha, Tokyo, Japan

[21] Appl. No.: 15,837

[22] Filed: Feb. 10, 1993

Related U.S. Application Data

[63] Continuation-in-part of Ser. No. 841,666, Feb. 21, 1992, abandoned.

[30] Foreign Application Priority Data

Feb. 22, 1991 [JP] Japan ..................... 3-048645

[51] Int. Cl.$^6$ .................... B01D 39/00; B01D 27/00; B01D 29/00
[52] U.S. Cl. .................. 210/496; 210/435; 210/446; 210/483; 210/503; 210/506
[58] Field of Search ................. 210/435, 446, 210/483, 496, 503, 505, 506, 508, 500.27, 500.29, 500.42; 428/304.4, 310.5, 307.3, 308.4

[56] References Cited

U.S. PATENT DOCUMENTS

| | | | |
|---|---|---|---|
| 4,246,107 | 1/1981 | Takenaka et al. | 210/806 |
| 4,366,068 | 12/1982 | Ostreicher et al. | 210/767 |
| 4,416,777 | 11/1983 | Kuroda et al. | 210/446 |
| 4,523,995 | 6/1985 | Pall et al. | 210/505 |
| 4,617,124 | 10/1986 | Pall et al. | 210/508 |
| 4,673,504 | 6/1987 | Ostreicher et al. | 210/500.22 |
| 4,880,548 | 11/1989 | Pall et al. | 210/767 |
| 4,915,839 | 4/1990 | Marinaccio et al. | 210/500.23 |
| 4,936,993 | 6/1990 | Nomura | 210/435 |
| 4,936,998 | 6/1990 | Nishimura et al. | 210/496 |
| 4,985,153 | 1/1991 | Kuroda et al. | 210/782 |
| 5,100,564 | 3/1992 | Pall et al. | 210/782 |
| 5,133,878 | 7/1992 | Gsell et al. | 210/496 |
| 5,164,087 | 11/1992 | Naoi et al. | 210/500.42 |
| 5,215,692 | 6/1993 | Hörl et al. | 210/500.37 |

FOREIGN PATENT DOCUMENTS

| | | |
|---|---|---|
| 0077633 | 4/1983 | European Pat. Off. . |
| 0331174 | 9/1989 | European Pat. Off. . |
| 56-53616 | 5/1981 | Japan . |
| 61-77752 | 4/1986 | Japan . |
| 63-200052 | 8/1988 | Japan . |
| 1-224325 | 9/1989 | Japan . |
| 1-224324 | 9/1989 | Japan . |
| 1-320064 | 12/1989 | Japan . |
| 1-320065 | 12/1989 | Japan . |
| 2238055 | 4/1991 | United Kingdom . |

OTHER PUBLICATIONS

European Search Report 92400462.5.

*Primary Examiner*—John Kim
*Attorney, Agent, or Firm*—Burns, Doane, Swecker & Mathis

[57] ABSTRACT

A filter for removing leukocytes and thrombocytes from a solution containing blood components, such as CRC, comprises a filter material having a first surface serving as an inlet surface and a second surface serving as an outlet surface. The outlet surface has a positive zeta potential greater than that of the inlet surface in an electrolyte solution having a pH value of 5.0 to 7.0.

5 Claims, 4 Drawing Sheets

LEUKOCYTE-REMOVING FILTER AND LEUKOCYTE-REMOVING APPARATUS FURNISHED THEREWITH

This is a continuation-in-part application Ser. No. 07/841,666, filed Feb. 21, 1992, abandoned.

BACKGROUND OF THE INVENTION

1. Field of The Invention

This invention relates generally to a leukocyte-removing filter and a leukocyte-removing apparatus furnished therewith. More specifically, it relates to a leukocyte-removing filter capable of removing leukocytes from a solution containing blood components while efficiently removing thrombocytes or blood platelets therefrom.

2. Description of The Prior Art

In recent years, blood transfusion has been changing from whole blood transfusion to component blood transfusion, so that a component medicine containing pure erythrocytes has been required. Generally, blood obtained from donors is fractionated into various components by centrifugation so that erythrocytic component is separated from other components in the form of a concentrated red cell, which will be hereinafter referred to as "CRC", to be transfused into patients who need erythrocytes. However, since such a CRC copiously contains other blood cells, such as leukocytes and thrombocytes, there are serious problems in that side effects tend to be caused by the components other than erythrocytes after transfusion. Particularly, side effects, such as non-hemolytic pyrogenic side effects, production of antileukocytic antibodies and graft v.s. host reaction, are often caused by leukocytes after transfusion. For that reason, leukocytes are usually removed from CRC by filtration. Furthermore, a case where transfusion is frequently repeated, it is desired to remove thrombocytes from CRC since it is required to prevent thrombocytes from producing antithrombocytic antibody.

Heretofore, in order to remove thrombocytes along with leukocytes, a filter of a small pore size (distances between fibers are small in a case where the filter comprises fibers) is used. However, when the pore size of the filter is decreased, the flow rate of blood passing through the filter decreases, so that there is the disadvantage in that the filtration and removal of leukocytes and thrombocytes take a long time.

It is therefore a principal object of this invention to provide a filter which can efficiently remove leukocytes together with thrombocytes by filtration or adsorption from a solution containing blood cells, such as CRC, and an apparatus furnished therewith.

SUMMARY OF THE INVENTION

In order to accomplish the aforementioned and other objects, a leukocyte-removing filter of this invention comprises a porous filter material having an inlet surface and an outlet surface having a zeta potential greater than that of the inlet surface in an electrolyte solution of a pH value of 5.0 to 7.0.

According to one aspect of this invention, a filter for removing leukocytes and thrombocytes from a solution containing blood components comprises a filter material having a first surface serving as an inlet surface for introducing the solution into the interior thereof, and a second surface serving as an outlet surface for discharging a filtrate to the exterior, the second surface having a zeta potential greater than that of the first surface at a pH value of 5.0 to 7.0.

The zeta potential of the second surface is preferably a positive zeta value, further preferably not less than 3 mV, and zeta potential of the first surface is preferably not greater than zero. The filter material may be composed of a plurality of filter layers or one filter layer. The filter material may be made of cellulose fibers. Alternatively, the filter material may be a porous body made of polyvinyl alcohol cross-linked with formaldehyde or polyurethane.

According to another aspect of this invention, an apparatus for removing leukocytes and thrombocytes from a solution containing blood components comprises: a container having an inlet for introducing the solution containing blood components into the interior thereof, and an outlet for discharging a filtrate to the exterior and a filter housed within the container, the filter being composed of a filter material having a first surface on the side of the inlet, and a second surface on the side of the outlet, the second surface having a zeta potential greater than that of the first surface at a pH value of 5.0 to 7.0.

BRIEF DESCRIPTION OF THE DRAWINGS

This invention will be understood more fully from the detailed description given herebelow and from the accompanying drawings of the preferred embodiments of the invention. However, the drawings are not intended to imply limitation of the invention to a specific embodiment, but are for explanation and understanding only.

In the drawings.

DESCRIPTION OF THE PREFERRED EMBODIMENT

According to this invention, a leukocyte-removing filter comprises a porous filter material having an inlet surface and an outlet surface which has a zeta potential greater than that of the inlet surface in an electrolyte solution having a pH value of 5.0 to 7.0. By using such a porous filter material, it is possible to efficiently remove thrombocytes without reducing the pore size of the porous filter material, so that it is possible to efficiently and quickly perform filtration and removal of leukocytes and thrombocytes.

In this specification, the term "porous filter material" means a filter material having a plurality of fine pores which establish communications between the opposite surfaces thereof. As a leukocyte-removing filter of this invention, various porous filter materials may be used, provided that they have liquid permeability and an average pore size for allowing selective removal of leukocytes. There is no specific limitation to the shapes and communication state of the pores. There is also no specific limitation to thickness, material, shape, size and so forth of the filter material. The filter material may be made in various forms, such as film, sheet, membrane, plate, block, fiber and particle. The filter material may be made of either organic or inorganic material, and either a natural material, synthetic material (resin) or a semisynthetic material (resin). For example, the porous filter material of this invention may include a porous body of organic or inorganic fibers made of a natural, synthetic, semisynthetic or reproduced material; organic or inorganic foams; an organic or inorganic porous body having a plurality of pores formed by elution of pore components, sintering, stretching or perforating; or a porous body filled with or connected to organic or inorganic fine particles or fine pieces. For example, porous filter material made of fibers may be organic or inorganic short fibers, slivers or long fibers. The filter material may be made in various forms, such as a simple packing material of fiber, an aggregation, non-woven fabric, and knit or woven fabric. According to this invention, in a case where the filter materials are made of fibers, they are preferably cellulose fibers, such as Egyptian cotton, or regenerated cellulose fibers, and in a case where the filter materials are porous bodies, they are preferably made of polyvinyl alcohol crosslinked with formaldehyde or polyurethane.

In this specification, the term "zeta potential" means a value represented by the voltage which corresponds to a relative potential on an interface of a solid-liquid dispersion system, i.e. a solution in which solid particles are suspended, when it is assumed that the potential in the solution is zero. Methods for measuring zeta potential are broadly divided into those using a electrophoresis method, an electroendosmosis method, a flow potential method and a precipitation potential method. In the preferred embodiments of this invention, a method using a flow potential method was used. As is well known, in this method, zeta potential is determined by measuring electrical outputs caused by mechanical energy applied to the dispersion system. Methods for measuring zeta potential using a flow potential method, and systems using same are described in "Membrane Experiment Method" by Masayuki Nakagaki (Kitami Shobo Co., Ltd.), pages 93–95, JP-A-61-77752 and JP-A-63-200052. In the preferred embodiments of this invention, Shimazu Flow Potential Measuring Apparatus ZP-10B (produced by Shimazu Seisakusho Co., Ltd.) was used. By using the measured potential in Helmholts-Smoluchowski's formula as expressed by the following formula I, zeta potential was calculated.

Zeta Potential $(mV) = (4\pi\eta/\epsilon) \times (Es\ \lambda/P)$    ... (1)

wherein $\eta$ is coefficient of kinematic viscosity of the solution, $\epsilon$ is dielectric constant of the solution, $\lambda$ is electrical conductivity of the solution, and P is pressure applied to the solution in order to cause the solution to flow.

According to this invention, if the porous filter material to be used has a positive zeta potential in an electrolyte solution having a pH value of 5.0 to 7.0, it may be used as a material of the leukocyte-removing filter as it stands. On the other hand, if the porous filter material has a negative zeta potential in the aforementioned solution, it may be used as a material of the leukocyte-removing filter after it is treated to change its zeta potential to a positive value. Furthermore, even if the zeta potential is a positive value, it may be treated to further increase the positive value. In order to obtain a porous filter material having a positive zeta potential, various methods may be used. For example, there is a method for using a filter forming material having a positive zeta potential by itself; a method for forming a filter material after causing a substance for making zeta potential positive, for example, a substance having a cationic functional group, such as amino group, to be contained in or connected to the filter forming material; a method for forming a filter material from a mixture of a filter forming material and other material having a positive zeta potential; or a method for performing a treatment for causing zeta potential of a filter material to be changed to positive after forming the filter material.

Specifically, there is a method for allowing a porous filter material made of a cellulose fiber or an organic polymer to react with a reactive (polymerizable) monomer having a positive zeta potential, such as a method for forming a filter material of cellulose fibers which have been allowed to react with a polyfunctional reactive quaternary ammonium to have a positive zeta potential, a method for forming a filter material by graft polymerizing a porous filter material of a porous membrane or fibers made of polypropylene with vinylpyridine by plasma polymerization, allowing the graft-polymerized porous filter material to react with benzylchloride, and then quaternizing an amino group of pyridine, and a method for polymerizing a monomer capable of applying a positive zeta potential, such as allyl amine hydrochloride salts, with a porous filter material made of an organic polymer; a method for directly forming a porous filter material of fiber, membrane, foam or other porous structures from a polymer or copolymer after producing the polymer or copolymer of polymerizable monomers having a cationic group; a method for treating a surface of a porous filter material by using the aforementioned polymer or copolymer having the cationic group; or a method for forming a porous filter material by binding glass fibers or glass particles with a binder having a positive zeta potential.

As the aforementioned quarternary ammonium compounds, there are 2-(meth)acryloyloxy alkyltrialkyl ammonium halides, such as 2-(meth)acryloyloxy ethyltrimethyl ammonium chloride, 2-(meth)acryloyloxy ehyltriethyl ammonium chloride, 2-(meth)acryloyloxy ethylpropyl ammonium chloride, 2-(meth)acryloyloxy ethyltrimethyl ammonium bromide, 2-(meth)acryloyloxy ethyltriethyl ammonium bromide, and a compound represented by the following formula II. This compound will be hereinafter referred to as "compound A".

It should be noted that a leukocyte-removing filter of this invention must have a positive zeta potential (including zero), i.e. a value of not less than 0 mV, preferably not less than 3 mV. If the zeta potential is less than zero, although leukocytes may be removed, the removal ratio of thrombocytes is low. There is no specific limitation to the maximum value of zeta potential. However, in practice, it is difficult to obtain a porous filter material having zeta potential of not less than 25 mV.

Although there is no specific limitation to the shape and structure of an apparatus furnished with a leukocyte-removing filter of this invention, and to a method for mounting or arranging the filter on the apparatus, the filter may be used in conventional types of apparatus. That is, the shape or the like of the apparatus may be suitably selected in accordance with the kind, material, shape, use of the porous filter material. A leukocyte-removing filter of this invention may comprise one or more porous filter layers. In a case where one porous filter layer is used, it has at least one surface on which zeta potential is a positive value in an electrolyte solution having a pH value of 5.0 to 7.0. In a case where a plurality of porous filter layers are used, at least one of the porous filter layers has a surface on which the zeta potential is a positive value in an electrolyte solution having a pH value of 5.0 to 7.0. Preferably, the filter layer having such a surface is arranged on the outlet side.

Referring now to the drawings, the preferred embodiments of a leukocyte-removing filter and a leukocyte-removing apparatus of this invention will be described below.

Figure 1:
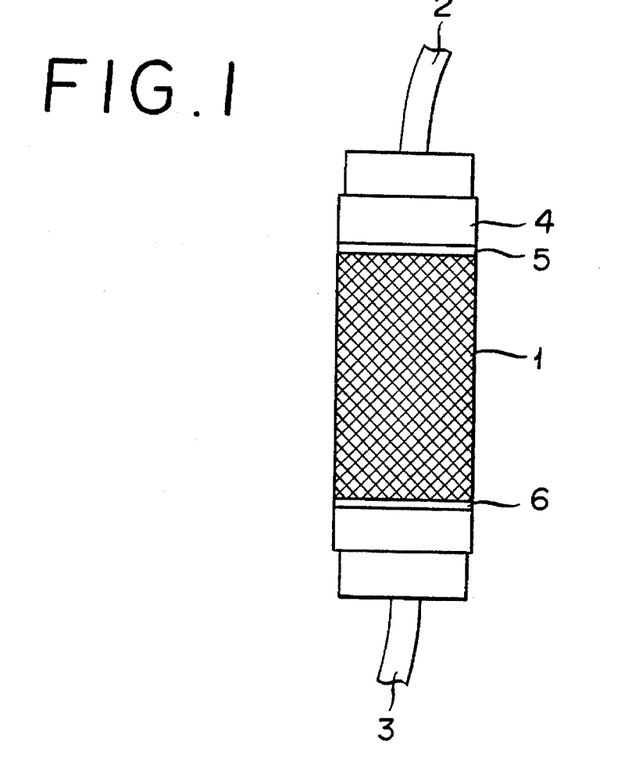
FIG. 1 is a schematic view of the first preferred embodiment of an leukocyte-removing apparatus, according to this invention.

FIG. 1 shows the first preferred embodiment of a leukocyte-removing apparatus, according to the present invention. In this embodiment, a porous filter material 1 (e.g. fibrous or granulated filter material) which has a positive zeta potential in an electrolyte solution having a pH value of 5.0 to 7.0, is housed within a cylindrical column 4 having a blood inlet 2 and a blood outlet 3. The porous filter material 1 is arranged between a prefilter 5 for preventing micro aggregated substances from being introduced into the porous filter material, and a mesh 6 for preventing the porous filter material from moving downwards.

Figure 2:
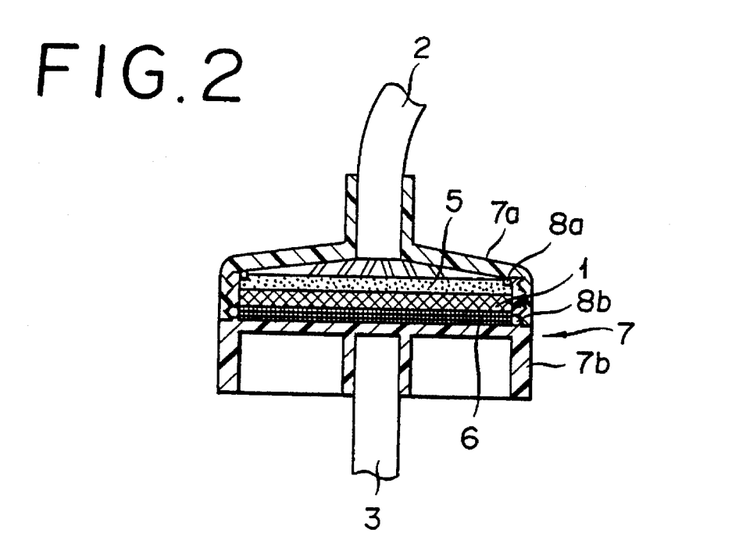
FIG. 2 is a schematic view of the second preferred embodiment of an leukocyte-removing apparatus, according to this invention.

FIG. 2 shows the second preferred embodiment of a leukocyte-removing apparatus, according to the present invention. In this embodiment, a porous filter material 1 in the form of a sheet, film, membrane or plate, which material has a positive zeta potential in an electrolyte solution having a pH value of 5.0 to 7.0 is arranged in a holder 7 having a blood inlet 2 and a blood outlet 3 between the prefilter 5 made of synthetic resin, such as polypropylene and polyethylene, and the mesh 6. Gels or microggregates in blood is initially removed by positioning the prefilter 5 at the most inlet side, so clogging of the porous filter 1 at the outlet side can be prevented. The holder 7 is made of synthetic resin, such as polypropylene, MBS, polymethyl methacrylate and carbonate, and it comprises an upper holder member 7a and a lower holder member 7b which engage with each other in the form of a screw via an O-ring 8b made of silicone rubber. The prefilter 5 is pressed downwards by a pressing portion of the upper holder member 7a via an O-ring 8a.

Figure 3:
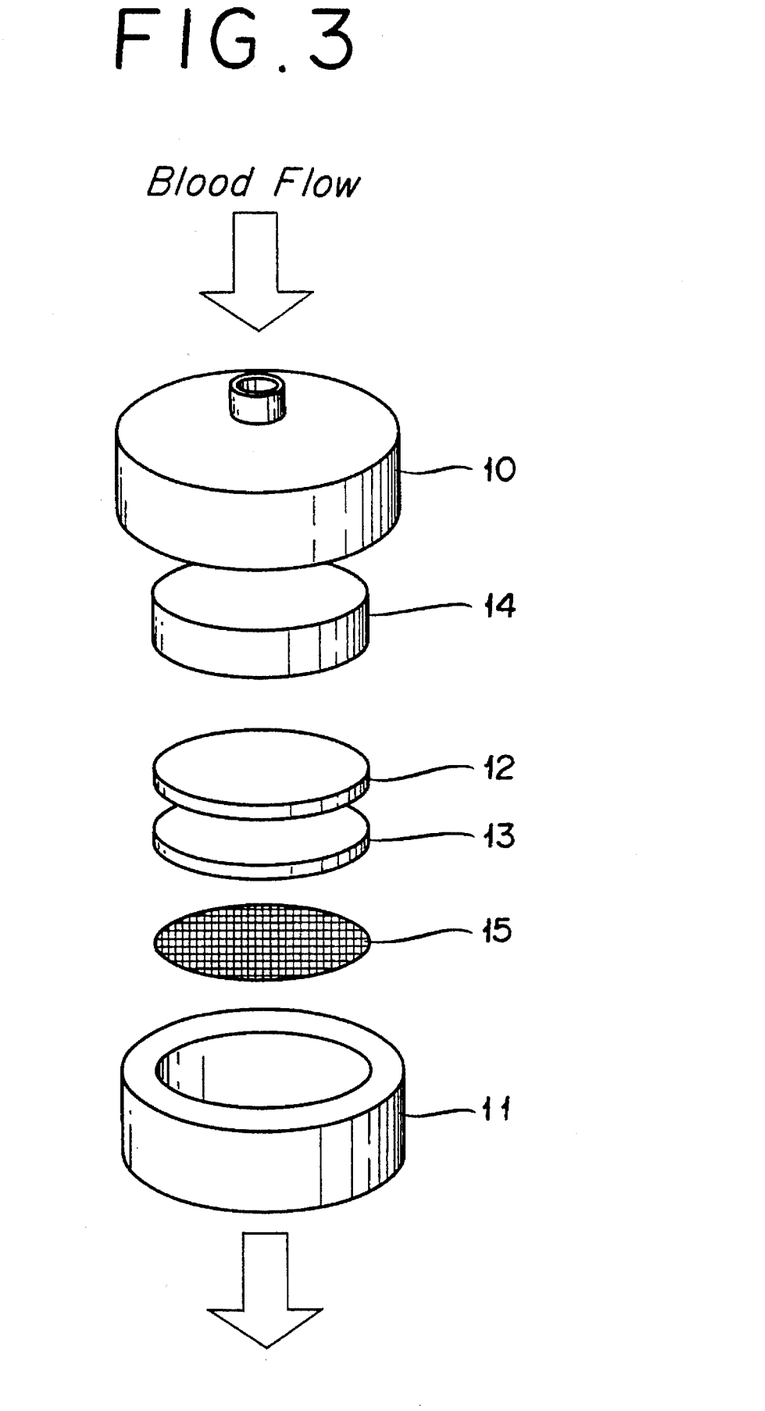
FIG. 3 is a perspective view of the third preferred embodiment of an leukocyte-removing apparatus, according to this invention.

FIG. 3 shows the third preferred embodiment of a leukocyte-removing apparatus, according to the present invention. In this embodiment, the leukocyte-removing apparatus comprises a filter housing composed of a upper shell 10 and a lower shell 11, and first and second main filters 12 and 13 housed within the filter housing. The first main filter 12 is arranged on the upstream side relative to the blood flow and has a surface having a negative zeta potential. The second main filter 13 is arranged on the downstream side thereto and has a surface having a positive zeta potential. A prefilter 14 comprising a lamination of non-woven fabric is arranged on the upstream side of these main filters 12 and 13, and a spacer 15 for preventing the filters from tightly contacting the inner wall of the housing is arranged on the downstream side thereof.

As a material for the prefilter 14, polyester non-woven fabric is preferable and it may be one layer or laminated to multi-layers. Further, the prefilter 14 itself is preferable to have 5 to 25% of blood corpuscle renoval ratio. If it is less than 5%, there is danger that gels or microaggregates in the blood leaks, and if it is more than 25%, the prefilter 1 timeclogs.

Furthermore, by making a leukocyte-removing filter of the present invention hydrophilic in a well-known manner, it is easy for blood preparation to infiltrate into the filter, and it is possible to prevent the partial air blocking of the filter.

The effectiveness of a leukocyte-removing filter of this invention will be understood from the following Examples.

EXAMPLE 1

A solution was prepared by dissolving 510 g of a cationizing agent (Trademark "Cationon UK" commercially available from Ipposha Yushi Kogyo, Co., Ltd.) and 77 g of sodium hydroxide in 3,413 ml of distilled water. After 170 g of cellulose fibers (Egyptian cotton) was dipped in this solution at 80° C. for 60 minutes, the cellulose fibers were removed from the solution and dried at 80° C. Then, 2 g of the treated cellulose fibers were arranged in a flow potential measuring cell of a Shimazu Flow Potential Measuring Apparatus ZP-10B, and the flow potential thereof was measured at a temperature of 20° ±5 ° C. by using 1 millimole KCl solution (pH 6±1) as the flow medium. As a result, the value Es/P (flow potential/pressure applied to the solution in order to cause the solution to flow) was $3.5 \times 10^{-5}$. This value was used in the aforementioned formula I with the coefficient of kinematic viscosity $\eta=0.009142$, the dielectric constant $\epsilon=78.89$ and the electrical conductivity $\lambda=1.31 \times 10^8$ to obtain the zeta potential of the cellulose fibers. As a result, its zeta potential was 6.7 mV.

The cylindrical column (inner diameter=15.7 mm) of the leukocyte-removing apparatus of FIG. 1 was filled with 1,625 g of the aforementioned cellulose fibers along with the prefilter 5 having 0.8 mm of thickness and the mesh 6 so that the length of the filter layer was 42.0 mm and density of the cellulose fibers was 0.20 g/cm$^3$.

Then, 400 ml of human blood was collected in a blood bag (Trademark "Terumo Double Bag" commercially available from Terumo Kabushiki Kaisha) while it was anti-coagulated with titrate-phosphate dextrose (CPD), and centrifugation of this human blood was performed at a rate of 3,000 rpm for 10 minutes. Thereafter, 150 ml of blood plasma which is a supernatant was taken in a transfer bag. An erythrocytes suspension was prepared by adding about 150 ml of physiological saline solution to the remaining CRC so that hematocrit becomes 50%. Then, 25 ml of this suspension was introduced into the leukocyte-removing apparatus via the blood inlet 2, and the time required for the whole suspension to be discharged from the blood outlet 3 was measured. Furthermore, the numbers of leukocytes and thrombocytes were measured by a counter ("Sysmex NE-6000" commercially available from Toa Iyodenshi Co., Ltd.), and the removal ratios of leukocytes and thrombocytes were calculated by the following formula.

(Number of Each Type of Blood Cells Before Filtration Number—of Each Type of Blood Cells After Filtration)×100/(Number of Each Type of Blood Cells Before Filtration)

As a result, the required time was 2 minutes 40 seconds, the removal ratio of leukocytes was 96%, and the removal ratio of thrombocytes was 97±3%.

As a reference, cellulose fibers (zeta potential= −23.9 mV) of the same type as that of the aforementioned embodiment were used without a cationizing treatment to determine, the time required for the whole suspension liquid to be discharged from the blood outlet 3, and the removal ratios of leukocytes and thrombocytes in the same manner as that of the aforementioned embodiment. As a result, the required time was 3 minutes, the removal ratio of leukocytes was 95% and the removal ratio of thrombocytes was 58±3%.

EXAMPLE 2

In 6 ml of an aqueous solution of saturated sodium hydroxide, 3 g of cellulose fibers and 15 ml of epichlorohydrin were add to allow a reaction at 50° C. for 2 hours. Then, the cellulose fibers were dipped in a methanol solution containing 0.2 moles of 4-aminopyridine to allow a reaction at 50° C. for 3 hours. Thereafter, the cellulose fibers were removed from the solution to be dipped in 500 ml of a methanol solution containing 2 moles of methyliodide to allow a reaction in a tightly sealed vessel at 30° C. for 24 hours. The zeta potential of the treated cellulose fibers was determined in the same manner as that of Example 1. As a result, it was +9.2 mV.

Then, the cylindrical column as shown in FIG. 1 was filled with 1.625 g of the obtained cellulose fibers (with a fiber density of 0.20 g/cm$^3$), and the measurement was performed in the same manner as that of Example 1. As a result, the required time was 3 minutes 40 seconds, the removal ratio of leukocytes was 85%, and the removal ratio of thrombocytes was 75.0%.

As a reference, the same test was performed with respect to untreated cellulose fibers having −23.9 mV of zeta potential. As a result, the required time was 3 minutes 55 seconds, the removal ratio of leukocytes was 87.1% and the removal ratio of thrombocytes was 52.2%.

EXAMPLE 3

In 100 ml of water, 1 g of a porous body (1.3 mm in thickness, about 10 μm in average pore diameter) of polyvinyl alcohol cross-linked with formaldehyde was dipped, and 2.5 ml of nitric acid solution containing 0.1 mol/liter cerium ammonium nitrate, which nitric acid solution was prepared by dissolving cerium ammonium nitrate in 1N nitric acid, was added thereto. In this solution, 5 g of acrylamide was further dissolved to allow polymerization under an atmosphere of nitrogen at 40° C. for 1 hour.

The zeta potential of the obtained porous body was determined in the same manner as that of Example 1. As a result, it was +5.9 mV.

A disc of 25 mm diameter was punched out of this porous body. This disc was placed together with a prefilter 5 of 0.8 mm thickness and a mesh 6 in a holder shown in FIG. 2, and the same test as that of Example 1 was performed. As a result, the required time was 3 minutes 16 seconds, the removal ratio of leukocytes was 93.3%, and the removal ratio of thrombocytes was 91.4%.

As a reference, the same test was performed with respect to untreated porous body of polyvinyl alcohol cross-linked with formaldehyde (zeta potential=−22.8 mV). As a result, the required time was 2 minutes 29 seconds, the removal ratio of leukocytes was 92.0%, and the removal ratio of thrombocytes was 65.5%.

Furthermore, the pore size of the porous body was measured by a mercury intrusion method.

EXAMPLE 4

A porous filter of polyurethane (0.5 mm in thickness, about 10 μm in average pore diameter) was washed with methanol in a Soxhlet apparatus for 8 hours, and then, it was irradiated with cold plasma (argon, 0.2 Torr) for 20 seconds. Subsequently, the porous filter together with 4-vinyl pyridine gas (0.5 Torr) were introduced into a reaction vessel, and graft polymerization of the surface was performed. In a solution containing 0.1M of benzyl chloride, the surface-grafted filter was quarternized at 55° C. for three hours. Thus, a porous filter of polyurethane having a N-benzyl pyridinium chloride group on the surface thereof was obtained.

The zeta potential of this porous filter was determined in the same manner as that of Example 1, and it was +46.8 mV. Furthermore, the same test as that of Example 1 was performed. As a result, the required time was 4 minutes 50 seconds, the removal ratio of leukocytes was 99.89%, and the removal ratio of thrombocytes was 98.84%.

EXAMPLE 5

In the same manner as that of Example 4, the same porous filter of polyurethane was graft polymerized, and quarternized in a methanol solution containing 0.1M of ethyl bromide at 50° C. for 16 hours to produce a porous filter of polyurethane having a triethyl ammonium bromide group on the surface thereof.

The zeta potential of this porous filter was determined in the same manner as that of Example 1. As a result, the required time was 4 minutes 25 seconds, the removal ratio of leukocytes was 99.73%, and the removal ratio of thrombocytes was 99.10%.

As a reference, with respect to a untreated porous filter of polyurethane used as a substance in Examples 4 and 5, zeta potential was determined. As a result, it was −40.0 mV. Furthermore, this untreated porous filter of polyurethane was tested in the same manner as that of Example 1. As a results, the required time was 4 minutes 33 seconds, the removal ratio of leukocytes was 91.4%, and the removal ratio of thrombocytes was 5.1%.

Example 6

Two porous filters of polyurethane (0.5 mm in thickness, 25 mm in diameter, about 15 μm in average pore diameter, zeta potential=−30 mV, removal ratio of leukocytes=about 80%) were prepared. One of these porous filters was graft polymerized with glycidyl acrylate, and then, the same cationizing agent as that of Example 1 was fixed thereto. The zeta potential of the obtained porous filter was +7.9 mV. In the same manner of Example 3, the obtained porous filter was arranged on the blood outlet side in the holder of FIG. 1 to be used as a main filter, and another porous filter was arranged on the blood inlet side in the holder. CRC which contains 84.8×10$^2$/μl of leukocytes and which has 73% of hematocrit value was filtered at a constant speed of 0.5 ml/min·cm$^2$ to determine the removal ratios of leukocytes and thrombocytes.

As a result, the removal ratio of leukocytes was 9.98%, and the removal ratio of thrombocytes was 99.90%. Furthermore, there was little blinding in the main filter after filtration for 15 minutes. In Examples 4, 5 and 6, the pore size was measured by the same method as that of Example 3.

EXAMPLE 7

Relationship Between Zeta Potential and Removal Ratios of Leukocytes and Thrombocytes A porous filter of polyurethane (0.5 mm in thickness) having about 30 to 60% of the removal ratio of leukocytes in this thickness and −30 mV of zeta potential, was graft-polymerized with a glycidyl acrylate. Then, a cationizing agent (Trademark "Cationon UK" commercially available from Ipposha Yushi Kogyo, Co., Ltd.) was fixed thereto to obtain a filter of +7.9 mV in zeta potential. The leukocyte-removing capacity of the obtained filter was compared with that of an untreated porous filter which was the same as the porous filter of polyurethane except that the aforementioned treatment was not carried out. These porous filters were stamped out to prepare test samples of 25 mm in diameter and 0.5 mm in thickness. These test samples were set in a filter holder (NUCLEPORE 25 mm HOLDER). Using these test samples, a fresh whole blood, a concentrated red cell, and a leukocyte-suspended solution were allowed to pass through the respective test samples at a flow rate of 0.5 ml/min·cm² for 10 minutes. The results are shown in Table 1.

TABLE 1

1: Fresh Whole Blood

|  | Conc. of Leukocytes (10E2/μl) | Conc. of Platelets (10E4/μl) | Conc. of Red blood cells (10E4/μl) |
| --- | --- | --- | --- |
| Before Filtration | 38.5 | 16.7 | 440 |
| Untreated Membrane | 13.5 | 15.9 | 442 |
| Cationized Membrane | 0.2 | 0.4 | 441 |

2: Concentrated Red Cell

|  | Conc. of Leukocytes (10E2/μl) | Conc. of Platelets (10E4/μl) | Conc. of Red blood cells (10E4/μl) |
| --- | --- | --- | --- |
| Before Filtration | 39.5 | 6.5 | 555 |
| Untreated Membrane | 26.6 | 5.9 | 554 |
| Cationized Membrane | 0.7 | 0.2 | 556 |

3: Leukocyte-Suspended Solution

|  | Conc. of Leukocytes (10E2/μl) | Conc. of Platelets (10E4/μl) |
| --- | --- | --- |
| Before Filtration | 48.7 | 5.2 |
| Untreated Membrane | 8.7 | 2.9 |
| Cationized Membrane | 0.1 | 0.0 |

Zeta Potential

| Untreated Membrane: | −30.2 mV |
| --- | --- |
| Cationized Membrane: | +7.9 mV |

From Table 1, it was found that the concentration of leukocytes in the filtrate filtered by the cationized filter was about 1/40 to 1/80 times smaller than that filtered by the untreated filter, and that the concentration of platelets in the filtrate filtered by the cationized filter was about 1/20 to 1/40 times smaller than that filtered by the untreated filter. These untreated and cationized filters were observed under an electron microscope. From this observation, it was found that in the case of the untreated filter, only leukocytes did not pass through the pores of the porous filter and were trapped therein. On the other hand, it was found that in the case of the cationized filter, a plurality of leukocytes, the number of which is greater than that trapped in the pore, adhered to the surface of the filter. In this case, it was also found that although platelets also adhered thereto, the amount of red blood cells adhered thereto was less than that of the adhering platelets. From these results, it would be understood that by cationizing the filter to make the zeta potential thereof positive, although the performance for capturing leukocytes and platelets is improved, there is no influence on the collection of red blood cells It was also found that by cationizing the filter, the starting time decreased and the fluid passage in the filter was evenly formed.

EXAMPLE 8

Advantages of Combination of Untreated Porous Body and Cationized Porous Body

Figure 4:
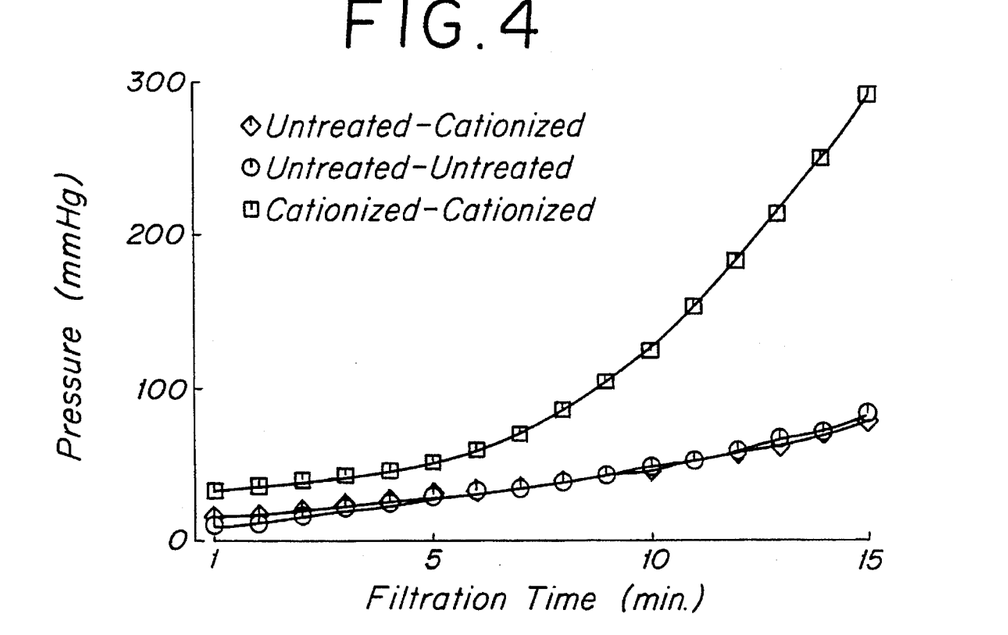
FIG. 4 is a graph showing the variation of the pressure applied to the leukocyte-removing filter, relative to filtration time.
Figure 5:
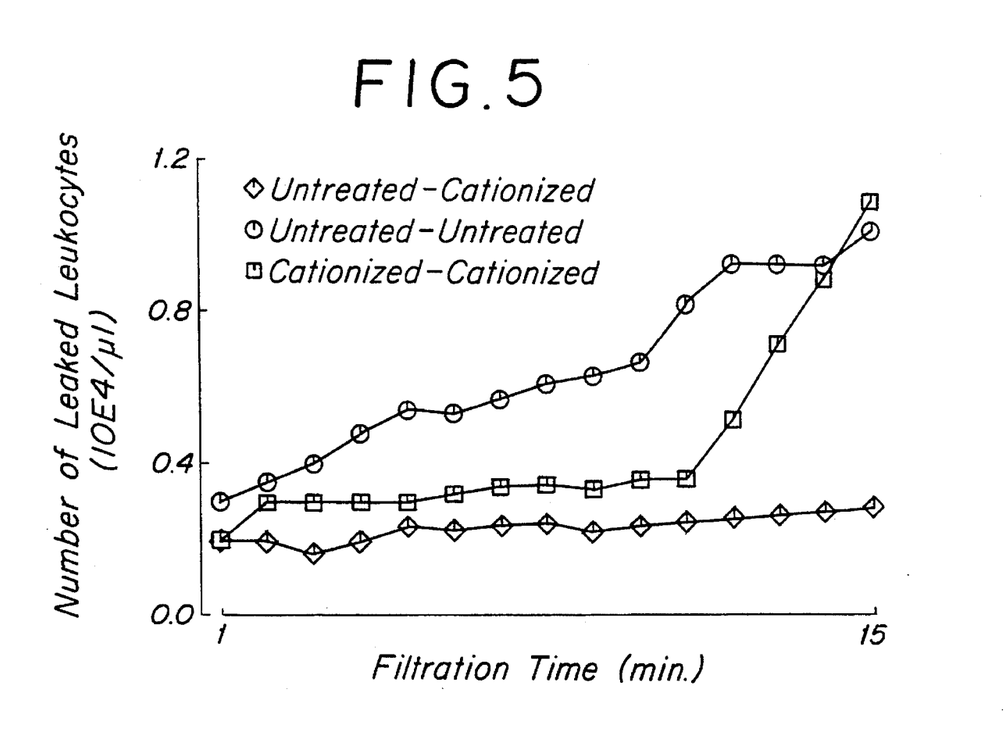
FIG. 5 is a graph showing the number of leaked platelets, relative to filtration time.
Figure 6:
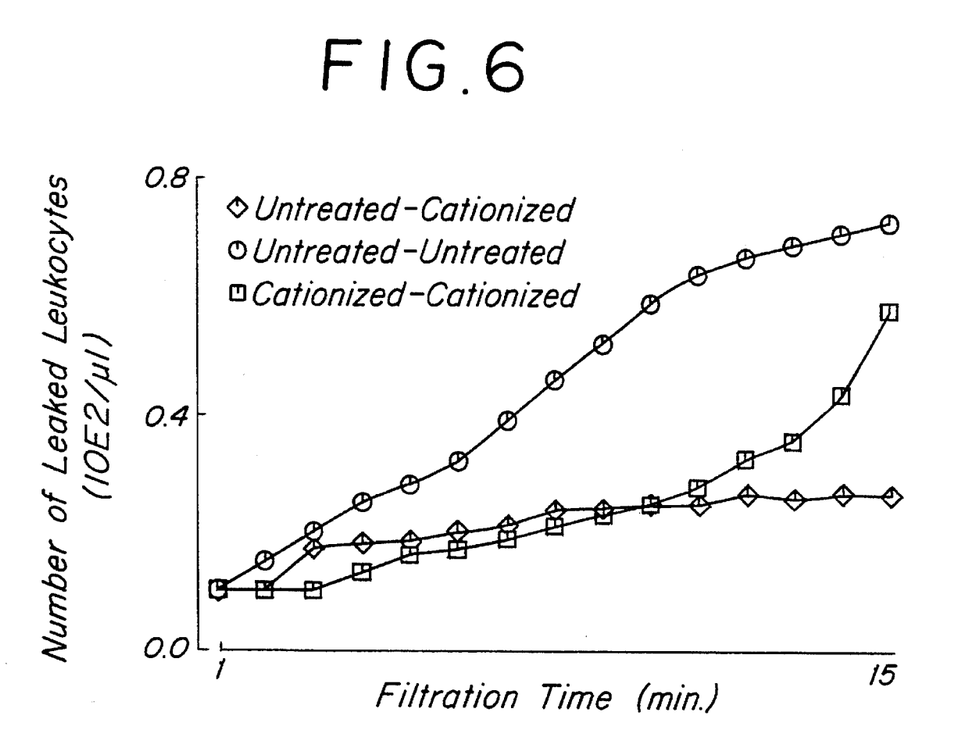
FIG. 6 is a graph showing the number of leaked leukocytes, relative to filtration time.

An untreated porous filter membrane of polyurethane (0.5 mm in thickness and 80% in removal ratio of leukocytes) was arranged upstream, and a porous filter membrane of polyurethane which was cationized in the same manner as that of Example 7 to cause the zeta potential to be +7.9 mV, was arranged downstream to produce a lamination type filter. The performance of this lamination type filter was compared with those of another combination. That is, three combinations of (a) untreated-cationized (the present invention), (b) untreated-untreated (comparative example), and (c) cationized-cationized (comparative example) were prepared. These filters were set in a filter holder of 25 mm in diameter. A concentrated red cell solution containing leukocytes of 84.8×10² particles/μl and having a hematocrit value of 73% was allowed to pass through the respective filters at a constant flow rate of 0.5 ml/min·cm² for 15 minutes, and the numbers of the leaked leukocytes and platelets in the filtrate and the pressure applied to the filter were measured every one minute. These results are shown in FIGS. 4, 5 and 6. It was found from FIG. 4 that in the cases of the combinations (a) and (b), the pressure applied to the filter was substantially the same, so that there was no excessive pressure to the filter when only one filter membrane was cationized. In respect of the numbers of the leaked leukocytes and platelets, in the case of the combination (b), the leakage increased in accordance with the passage of time, and in the case of the combination (a), it was stable as compared with the case of the combination (b). On the other hand, in the case of the combination (c), the pressure increase was large after the passage of 5 minutes, and in response to this, the numbers of the leaked leukocytes and platelets increased abruptly. This is because excessive pressure is applied to the blood passages in the porous body limited due to blinding, which decreases the opportunity of the leukocytes and platelets in the blood of contacting the filter and allowing the captured leukocytes and platelets to be removed from the filter. As the aforementioned results, it was found that by combining an untreated porous body and a cationized porous body, the filter could have a higher capacity for capturing leukocytes and platelets and a structure capable of processing a large amount of filtration.

In Examples 7 and 8, the prefilter was not used, because fresh blood or leukocyte-suspended solution did not almost contain microaggregate and gell, so the prefilter was not necessary. Further, when stored blood (concentrated red cell) was filtered microaggregate or gel was filtered off prior to the experiments.

EXAMPLE 9

Fibrous Filter

Filtration capacities were tested in combinations of cellulose fibers (Egyptian cotton zeta potential: −20.6 mV), and cationized cellulose fibers (zeta potential: +7.2 mV) which were cationized in the same manner as that of Example 7. That is, (a) 1.5 g of untreated Egyptian cotton, (b) 1.5 g of cationized Egyptian cotton, (c) a combination of 1.0 g untreated Egyptian cotton on the upstream side and 0.5 g cationized Egyptian cotton on the downstream side, were evenly packed in a column (diameter 1.5 mm; length 42.0 mm), and 25 ml of a concentrated red cell (leukocytes 6500/μl, platelets 232000 μ, hematocrit 68%) stored for 10 days was filtrated by the respective filter at a difference in elevation of 70 cm. The results are shown in Table 2.

TABLE 2

| | Number of Leukocyte ($10^2/\mu l$) | Removal Ratio (%) | Number of Platelet ($10^4/\mu l$) | Removal Ratio (%) | Number of red blood cells ($10^4/\mu l$) | Filtration Time |
|---|---|---|---|---|---|---|
| B.F.* | 65.0 | — | 23.2 | — | 688 | — |
| (a) | 14.1 | 78.3 | 10.3 | 55.4 | 687 | 3'32" |
| (b) | 0.3 | 99.5 | 0.2 | 99.1 | 678 | 9'43" |
| (c) | 0.2 | 99.7 | 0.3 | 98.7 | 686 | 3'58" |

*B.F.= Before Filtration
(a) Untreated, (b) Cationized, (c) Untreated + Cationized From the aforementioned results, it was found that by using a cationized Egyptian cotton, the capacity for removing leukocytes and platelets was greatly enhanced, and that by combining an untreated Egyptian cotton with the cationized Egyptian cotton, the filtration time decreased to provide a filter having a good filtration efficiency.

As mentioned above, a leukocyte-removing filter and an apparatus furnished therewith, according to the present invention, can effectively remove thrombocytes from a solution containing blood components without reducing the pore size of the filter material.

What is claimed is:

1. A filter apparatus for removing leukocytes and platelets from a solution containing blood components, said apparatus comprising:

a container having an inlet for introducing said solution containing blood components into the interior thereof, and an outlet for discharging a filtrate to the exterior; and a filter housed within said container, said filter comprising a filter material having a first surface on the side of said inlet, and a second surface on the side of said outlet, said second surface having a zeta potential greater than that of said first surface at a pH value of 5.0 to 7.0, said first surface having a zeta potential not greater than zero and said second surface having a positive zeta potential, and wherein said filter material is an organic or inorganic foam having continuous pores.

2. A filter apparatus for removing leukocytes and platelets from a solution containing blood components, said apparatus comprising:

a container having an inlet for introducing said solution containing blood components into the interior thereof, and an outlet for discharging a filtrate to the exterior; and a filter housed within said container, said filter comprising a filter material comprising a porous body made of polyvinyl alcohol cross-linked with formaldehyde having a first surface on the side of said inlet, and a second surface on the side of said outlet, said second surface having a zeta potential greater than that of said first surface at a pH value of 5.0 to 7.0, said first surface having a zeta potential not greater than zero and said second surface having a positive zeta potential.

3. A filter apparatus for removing leukocytes and platelets from a solution containing blood components, said apparatus comprising:

a container having an inlet for introducing said solution containing blood components into the interior thereof, and an outlet for discharging a filtrate to the exterior; and a filter housed within said container, said filter comprising a filter material comprising a porous body made of polyurethane having a first surface on the side of said inlet, and a second surface on the side of said outlet, said second surface having a zeta potential greater than that of said first surface at a pH value of 5.0 to 7.0, said first surface having a zeta potential not greater than zero and said second surface having a positive zeta potential.

4. A filter for removing leukocytes and platelets from a solution containing blood components, said filter comprising a filter material comprising a porous body made of polyvinyl alcohol cross-linked with formaldehyde having a first surface on an inlet side, and a second surface on an outlet side, said second surface having a zeta potential greater than that of said first surface at a pH value of 5.0 to 7.0, said first surface having a zeta potential not greater than zero and said second surface having a positive zeta potential.

5. A filter for removing leukocytes and platelets from a solution containing blood components, said filter comprising a filter material comprising a porous body made of polyurethane having a first surface on an inlet side, and a second surface on an outlet side, said second surface having a zeta potential greater than that of said first surface at a pH value of 5.0 to 7.0, said first surface having a zeta potential not greater than zero and said second surface having a positive zeta potential.

* * * * *

UNITED STATES PATENT AND TRADEMARK OFFICE
CERTIFICATE OF CORRECTION

PATENT NO. : 5,498,336

DATED : March 12, 1996

INVENTOR(S) : Naoki KATSURADA et al

It is certified that error appears in the above-indentified patent and that said Letters Patent is hereby corrected as shown below:

In Column 4, line 51, delete "Cl" and insert -- C$\ell$ --.

In Column 4, line 51, delete "OHCl" and insert -- OHC$\ell$ --.

In Column 6, line 26, delete "1,625" and insert -- 1.625 --.

In Column 6, line 33, delete "titrate-" and insert -- citrate- --.

In Column 6, line 48, delete "Filtration" and insert -- Filtration- --.

In Column 6, line 49, delete "Number-of" and insert -- Number of --.

In Column 8, line 45, delete "ul" and insert -- u$\ell$ --.

In Column 8, line 50, delete "9.98%" and insert -- 99.98% --.

In Column 9, line 16, delete "ul" (three occurrences) and insert -- u$\ell$ -- (three occurrences).

UNITED STATES PATENT AND TRADEMARK OFFICE
CERTIFICATE OF CORRECTION

PATENT NO. : 5,498,336
DATED : March 12, 1996
INVENTOR(S) : Naoki Katsurada et al It is certified that error appears in the above-indentified patent and that said Letters Patent is hereby corrected as shown below:

In Column 9, line 24, delete "ul" (three occurrences) and insert -- u$\ell$ -- (three occurrences).

In Column 9, line 33, delete "ul" (two occurrences) and insert -- u$\ell$ -- (two occurrences).

In Column 9, line 61, after "cells" insert -- . --.

In Column 10, line 14, delete "ul" and insert -- u$\ell$ --.

In Column 10, line 65, delete "ul" and insert -- u$\ell$ --.

In Column 10, line 65, delete "u," and insert -- u$\ell$, --.

In Column 11, line 7, delete "ul" (three occurrences) and insert -- u$\ell$ -- (three occurrences).

Signed and Sealed this

Twenty-eighth Day of May, 1996

*Attest:*

BRUCE LEHMAN

*Attesting Officer*  *Commissioner of Patents and Trademarks*